United States Patent [19]

Gorman et al.

[11] Patent Number: 4,523,848

[45] Date of Patent: Jun. 18, 1985

[54] POLARISCOPE

[75] Inventors: Barry Gorman, Preston; Edwin J. Hearn, Birmingham, both of England

[73] Assignee: National Research Development Corporation, London, England

[21] Appl. No.: 423,309

[22] Filed: Sep. 24, 1982

[30] Foreign Application Priority Data

Oct. 1, 1981 [GB] United Kingdom ............... 8129655

[51] Int. Cl.³ ............................................. G01B 11/18
[52] U.S. Cl. ..................................... 356/368; 356/35; 356/369
[58] Field of Search ..................... 356/33, 34, 35, 365, 356/368, 369

[56] References Cited

U.S. PATENT DOCUMENTS 3,902,805  9/1975  Redner .

FOREIGN PATENT DOCUMENTS 1372868 11/1974 United Kingdom .
1390925  4/1975 United Kingdom .
1448520  9/1976 United Kingdom .
1469638  4/1977 United Kingdom .
1477478  6/1977 United Kingdom .
1496499 12/1977 United Kingdom .
1506570  4/1978 United Kingdom .

OTHER PUBLICATIONS

Blyumkina et al., "System for Automating Ellipsometric Measurements" *Opt. Spectrosc.* vol. 40, No. 3, pp. 339–340.

Photoelasticity by E. J. Hearn, published by Merrow in 1971 describes the basic theory of polarimetry on pp. 6 to 12 and 18.

*Primary Examiner*—Davis L. Willis
*Assistant Examiner*—Matthew W. Koren
*Attorney, Agent, or Firm*—Cushman, Darby & Cushman

[57] ABSTRACT

In a polariscope including first and second quarter wave plates arranged one on either side of a sample under test, first and second liquid crystal devices are provided adjacent the quarter wave plates and can be switched between two optical conditions to alter the polariscope between a plane polarized and a circularly polarized mode.

6 Claims, 5 Drawing Figures

POLARISCOPE

A polariscope is an instrument used to study the interference patterns produced for example when a stressed model of an engineering component made from an optically transparent material is viewed in polarised light, the stress causing the material to become birefringent. Both plane and circularly polarised systems are needed, and practical polariscopes have two quarter wave plates used to achieve the circularly polarised condition which can be manually or mechanically removed from the optical path or rotated by 45°. Since the two conditions are required alternately during the point-by-point study of the model, entailing perhaps many hundreds of removals and reinsertions of the quarter wave plates, the instrument is cumbersome and its use is tedious.

It is the object of the present invention to provide a polariscope in which the transfer between plane and circular polarisations can be achieved without physical removal of components.

According to the invention a polariscope comprises means to provide a beam of polarised light; first liquid crystal means which in a first state allows passage of light from the polarising means, and in a second state applies a 45° rotation to light from the polarising means; a first quarter wave plate; sample location means; a second quarter wave plate; second liquid crystal means which in a first state allows passage of light polarised perpendicular to the polarising axis of the polarising means, and in a second state applies a 45° rotation to light polarised perpendicular to said polarising axis; second polarising means parallel to or crossed with respect to the first polarising means; and switch means to cause the first and second liquid crystal means each to change between their first and second states.

The beam of polarised light can be provided either by an unpolarised light source and a polariser, or by a laser source.

In such a polariscope, when the liquid crystals are in their first states, light passing through them is unaffected, and the device is a circularly polarised polariscope. When the liquid crystals are in their second state, they apply rotations to the polarised light to cancel the effect of the two quarter wave plates (i.e. by rotating the plane of polarisation to align with the axes of the quarter wave plates) so that the device acts as a plane polarised polariscope.

In a modification, the analyser of the polariscope according to the invention is itself a variable liquid crystal device, either a series of conventional devices which may be switched in to provide varying angles of rotation, or a continuously variable device in which the angle of rotation varies with the applied voltage.

In a first form of the invention, the sample is a transparent photoelastic material, often a model of an engineering component, and light is transmitted through the sample to the second quarter wave plate. In a second form of the invention, the sample is opaque and may be an actual component coated with a reflective photoelastic material; in this use the apparatus is arranged so that light passing through the first quarter wave plate is reflected by the photoelastic material to the second quarter wave plate.

In the accompanying drawings, the prior art is described with reference to FIGS. 1 and 2 in which.

Figure 3:
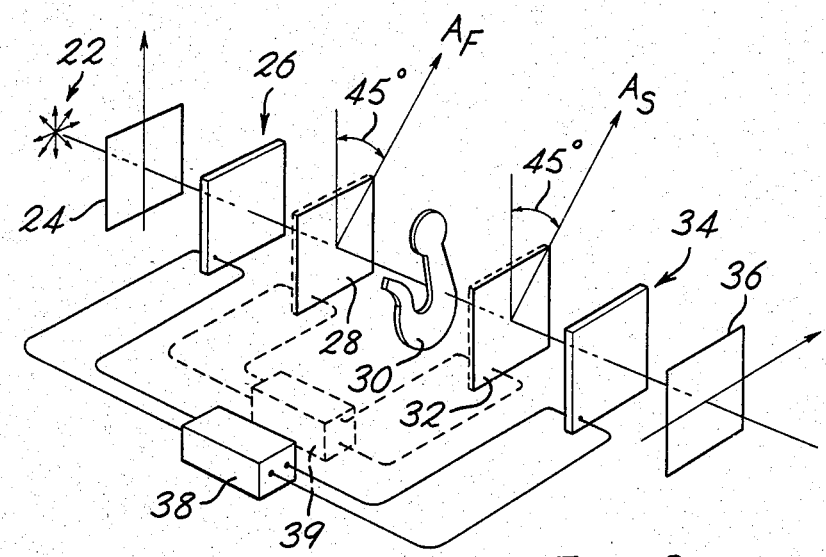
Figure 4:
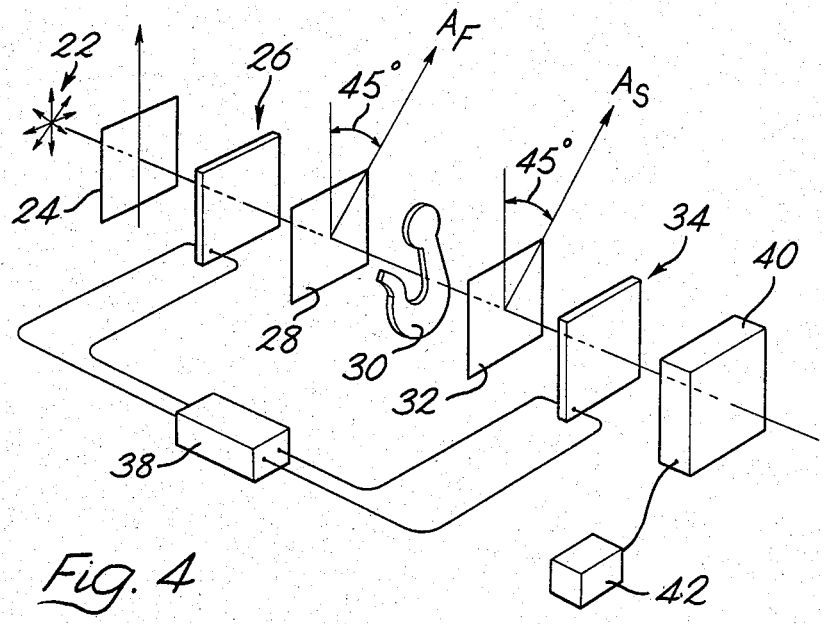
Figure 5:
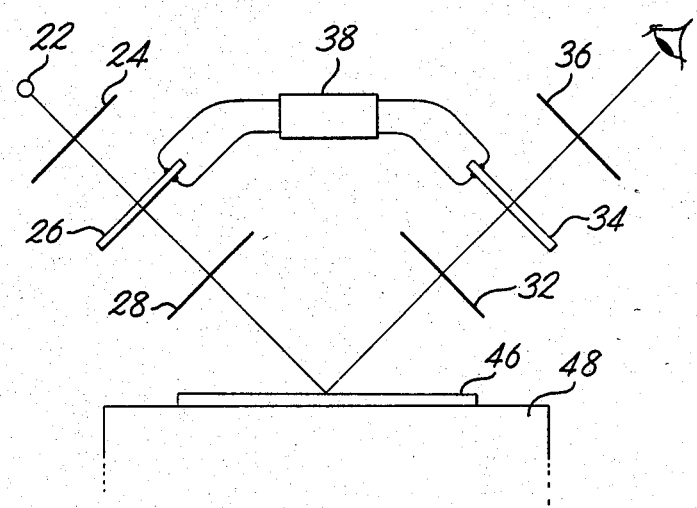

The invention will be described with reference to FIGS. 3, 4 and 5 in which:

FIG. 3 illustrates a transmission polariscope according to a first embodiment of the invention;

FIG. 4 illustrates a transmission polariscope in which compensation can be applied; and FIG. 5 illustrates a reflection polariscope according to the invention.

Figure 1:
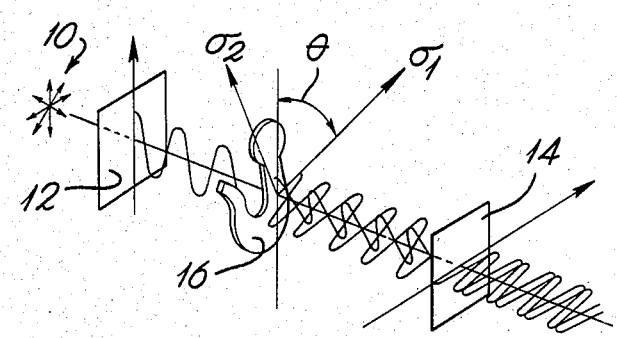
FIG. 1 illustrates a plane transmission polariscope.

Referring to FIG. 1 a prior art plane polariscope of the 'transmission' type consists of a light source 10, a polariser 12 having a vertical polarisation axis, and an analyser 14 having a horizontal polarisation axis. If a model of a component 16, made of birefringent material and shown here as hook shaped, is illuminated through the polariser 12 and is stressed, the incident light is resolved into components parallel to the two principal stresses $\sigma_1$ and $\sigma_2$, and one component is retarded with respect to the other, as illustrated, If the model is viewed through the analyser 14, isochromatic fringes are visible which by their spacing indicate the magnitude of stresses in the specimen. If the source 10 is a white light source, the fringes are coloured, while a monochromatic source produces black fringes on a coloured ground, but in both cases an additional series of black lines known as isoclinics are formed. An isoclinic is a locus of all points at which the principal stresses in a model have the same directions as the polarising axes of the polariscope. The presence of isoclinics confuses a monochromatic fringe pattern, but isoclinics are necessary to some parts of the measurement process since, when moved to a point by synchronous rotation of the polarising elements they indicate that the polarising axes are parallel with the principal stress directions at the point—a requirement before beginning the compensation process to determine stress magnitudes.

Figure 2:
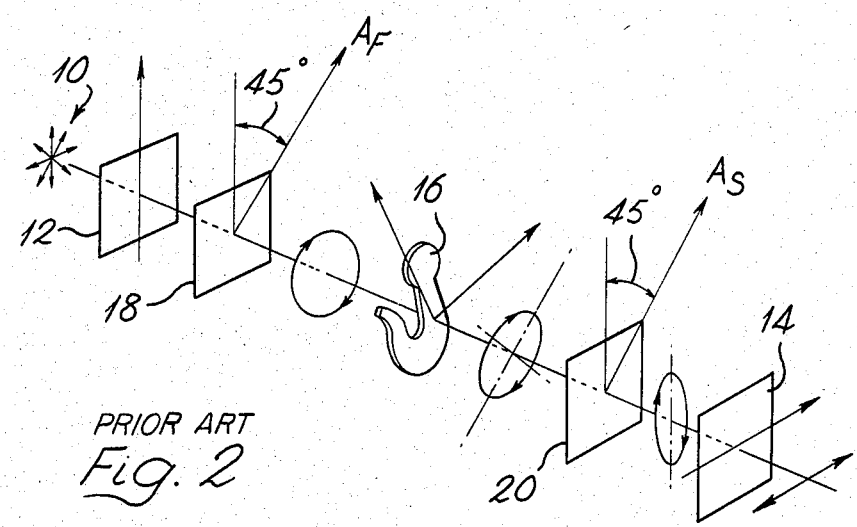
FIG. 2 illustrates a crossed circular transmission polariscope.

To remove isoclinics, a circularly polarised system is needed, as shown in FIG. 2. In addition to the components of a plane polariscope, there is a first quarter wave plate 18 between the polariser 12 and the model 16, having its "fast" axis $A_F$ at an angle of 45° to the vertical, and a second quarter wave plate 20 between the model 16 and the analyser 14, having its "slow" axis $A_S$ parallel to the fast axis of the first plate 18. In this arrangement, light is circularly polarised when it illuminates the model 16. The birefringent material of the model produces elliptically polarised light with the major axis aligned with the maximum principal stress, $\sigma_1$, as illustrated. The quarter wave plate 20 applies a rotation so that the major axis is vertical, i.e. perpendicular to the axis of analyser 14. The isochromatics are still visible, but the isoclinics are no longer present.

The two types of polariscope are described in "Photoelasticity" by E. J. Hearn, published by Merrow in 1971.

Since both types of polarising arrangement are essential in a practical polariscope, it is usual to provide an instrument in which the quarter wave plates 18, 20 are manually or mechanically removable or rotatable out of the light path. Thus the plates must be first placed in position then removed for each measuring point when a stressed model is investigated. Since measurements are often made at one hundred or more points, the process is clearly tedious.

A polariscope according to the invention and illustrated in FIG. 3 comprises a light source 22, a polariser 24 having a vertical axis, a first liquid crystal device (LCD) 26, a first quarter wave plate 28, a stressed model 30, a second quarter wave plate 32, a second liquid crystal device 34 and an analyser 36 having a horizontal axis of polaristion.

The polariscope is identical to that illustrated in FIG. 2, with the addition of the two LCDs 26, 34. Each LCD comprises a parallel-walled transparent cell containing a nematic liquid crystal material, the inner surfaces of the cell walls carrying transparent metal layers which can act as electrodes and which are connected to a voltage supply and switch circuit 38. The cells are arranged so that when the electrodes are activated by application of a voltage between the electrodes in each cell, polarised light passes through them undeviated, the quarter wave plates 28, 30 operate as in a conventional device, and the polariscope is circularly polarised. When the LCDs are unactivated, incident vertically polarised light is rotated through 45° by the first LCD 26 to pass undeviated through the quarter wave plate 28, to give plane polarised illumination equivalent to that in the FIG. 1 plane polariscope but at a different angle to the vertical, i.e. at 45°. Light passing through the stressed model 30 passes undeviated through the quarter wave plate 32, and is rotated 45° in the opposite direction by the second LCD 34, so that the polariscope operates as if it were plane polarised.

The alteration between plane and circular polarisation of the LCDs is thus achieved simply by operation of an electrical switch, an action requiring minimal effort and causing minimal disturbance in comparison with the physical movements required in a prior art instrument; the arrangement of the invention is particularly appropriate to the production of an automatically controlled polariscope. Usually one switch will control both LCDs.

It is not suggested that the combination of a quarter wave plate and a nematic liquid crystal to alter plane polarisation to circular polarisation is new. Such an arrangement is described in the specification of G.B. Pat. No. 1,390,925, but only in the context of an optical display device. Almost all applications of LCDs lie in the display field, and it is believed that this is the first time that an LCD has been used in a polariscope.

In a variation either or both of the quarter wave plates 28, 32 consist of an activated LCD. The or both plates are connected to a further voltage supply and switch circuit 39, shown dotted.

FIG. 4 illustrates en embodiment of the invention in which Tardy compensation can be applied. The polariscope is identical to that shown in FIG. 3 with the exception that the analyser 36 is replaced by a variable liquid crystal device 40 connected to a voltage supply and control circuit 42. The variable LCD 40 can be either a composite or cascade of several separate LCDs, each applying a small angular rotation, and switching in of successive LCDs giving a rotation equal to their sum, or can be a continuously variable LCD in which, by application of a varying voltage to a single, carefully constructed cell, the angle of rotation also varies continuously. Such devices are known and are described in the specifications of G.B. Pat. Nos. 1,372,868 and 1,506,570, but have not previously been used in a polariscope.

Tardy compensation in the prior art is carried out by first synchronously rotating the polariser and analyser in a plane polariscope until an isoclinic crosses a point of interest, and inserting the quarter wave plates to give a circular polariscope. Rotation of the analyser alone then appears to move the fringes, rotation by 180° corresponding to one fringe order. By measuring the rotation needed to cause a fringe of known order to coincide with the point of interest, the fraction of the order orginally coincident with that point can be determined. The process is described in the above referenced book "Photoelasticity" on page 18.

In the inventive arrangement, the rotation of the analyser alone, instead of being mechanical, is achieved electrically by use of the variable LCD 40. Control can be digital so that no angle measurement is needed, and it may be possible, by sufficiently fast switching, to extend conventional photoelastic techniques to the study of dynamic strains.

Clearly, the usual horizontal polarisation position of the analyser can be separately selected, and the device used as a conventional plane or circular polariscope as required. Also, during the setting-up procedure for Tardy compensation when the polariser and analyser are rotated synchronously, the LCDs must also be rotated in synchronism. In a variation, not illustrated, the polariser and analyser are also variable LCDs and are rotated electrically.

The arrangement can also be used to apply Senarmont compensation in which one LCD is switched to its inoperative state.

FIG. 5 illustrates a reflection polariscope; the components are identical to those in FIG. 3, but are arranged so that the beam from the quarter wave plate 28 is incident at an angle of 45° on a birefringent coating 46 on an opaque object under test 48. Light is reflected by the coating to the second quarter wave plate 32. In such a polariscope, the test object 48 is usually an actual component, and need not be of a photoelastic material.

It is an advantage of the invention that the LCDs can be fitted to currently available equipment, as well as incorporated in purpose-built polariscopes. In either case, the light source 10 is conventional. However, should a laser be used as the light source, the need for the first polariser may be avoided.

In some cases there is a time delay associated with the switching of a liquid crystal cell from one state to another, i.e. in converting a polariscope between plane and circular polarisation modes. If so, the anisotropy of a nematic liquid crystal cell under different applied voltages may be used by switching between applied voltages of different values instead of switching between zero and a single fixed value of voltage.

We claim:

1. A polariscope comprises means to provide an input beam of polarised light;

first liquid crystal means which in a first state allows direct passage of the polarised input beam and in a second state applies a 45° rotation to the polarised input beam;

a first quarter wave plate;

sample location means;

a second quarter wave plate;

second liquid crystal means which in a first state allows passage of light polarised perpendicular to the polarisation axis of the input beam and in a second state applies a 45° rotation to said light;

second polarising means parallel to or crossed with respect to the first polarising means; and switch means to cause the first and second liquid crystal means each to change between their first and second states.

2. A polariscope according to claim 1 in which the direction of polarisation of the second polarising means can be rotated with respect to the polarised input beam to angles intermediate the parallel and crossed positions.

3. A polariscope according to claim 2 in which the second polarising means is a liquid crystal device.

4. A polariscope according to claim 1 in which the components are provided in axial alignment to provide a transmission polariscope.

5. A polariscope according to claim 1 arranged so that light reflected by a sample in the sample location means is received by the second quarter wave plate, whereby a reflection polariscope is provided.

6. A polariscope according to claim 1 in which at least one quarter wave plate also comprises a liquid crystal device.

* * * * *